(12) United States Patent
Lee et al.

(10) Patent No.: US 10,238,583 B2
(45) Date of Patent: Mar. 26, 2019

(54) COMPOSITE POWDER IN WHICH JADE POWDER PARTICLES ARE IMPREGNATED IN POROUS POLYMER, COSMETIC COMPOSITION CONTAINING SAME AND MANUFACTURING METHOD FOR SAME

(71) Applicant: AMOREPACIFIC CORPORATION, Seoul (KR)

(72) Inventors: Hyun Suk Lee, Yongin-si (KR); Dong-Hyun Paik, Siheung-si (KR); Ga Young Cho, Yongin-si (KR); Hyoung June Kim, Yongin-si (KR); Hae Jin Jung, Yongin-si (KR); Dong Hyuk Jang, Yongin-si (KR); Yong Jin Kim, Yongin-si (KR); Lee Kyoung Kwon, Yongin-si (KR); John Hwan Lee, Yongin-si (KR); Sung-Wook Choi, Bucheon-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/576,125

(22) PCT Filed: Jun. 28, 2016

(86) PCT No.: PCT/KR2016/006882
§ 371 (c)(1),
(2) Date: Nov. 21, 2017

(87) PCT Pub. No.: WO2017/003149
PCT Pub. Date: Jan. 5, 2017

(65) Prior Publication Data
US 2018/0133115 A1   May 17, 2018

(30) Foreign Application Priority Data

Jun. 30, 2015 (KR) .......................... 10-2015-0092868
Jun. 27, 2016 (KR) .......................... 10-2016-0080232

(51) Int. Cl.
*A61K 8/19* (2006.01)
*A61K 8/02* (2006.01)
(Continued)

(52) U.S. Cl.
CPC ............ *A61K 8/0245* (2013.01); *A61K 8/022* (2013.01); *A61K 8/0279* (2013.01); *A61K 8/19* (2013.01);
(Continued)

(58) Field of Classification Search
CPC ........ A61K 8/022; A61K 8/0245; A61K 8/19; A61K 8/8152; A61K 8/8176; A61K 8/85; A61Q 19/00
See application file for complete search history.

(56) References Cited

U.S. PATENT DOCUMENTS

| 7,402,337 B2 | 7/2008 | Takaya et al. |
| 2007/0009560 A1 | 1/2007 | Golz-Berner |
| 2016/0053067 A1 | 2/2016 | Matsuno et al. |

FOREIGN PATENT DOCUMENTS

| EP | 1217035 A1 * | 6/2002 | ............... C08K 3/34 |
| EP | 2420221 A1 * | 2/2012 | ............ A61K 8/375 |

(Continued)

OTHER PUBLICATIONS

Yong (English Abstract of: CN103509474; Jan. 15, 2014). 1 page (Year: 2014).*

(Continued)

Primary Examiner — Ernst V Arnold
(74) Attorney, Agent, or Firm — Lucas & Mercanti, LLP (57) ABSTRACT

The present invention relates to a composite powder of jade powder and a porous polymer, and more specifically relates to a composite powder (jade sphere) in which jade powder particles are impregnated in a porous polymer, the composite powder being produced by spraying, in one step, a (Continued)

dispersion in which jade powder has been dispersed in a solution that dissolves porous polymers, and to a cosmetic composition containing the composite powder, and to a manufacturing method for the composite powder.

8 Claims, 8 Drawing Sheets

(51) Int. Cl.
    *A61Q 19/00*     (2006.01)
    *A61K 8/81*     (2006.01)
    *A61K 8/85*     (2006.01)

(52) U.S. Cl.
    CPC .......... *A61K 8/8147* (2013.01); *A61K 8/8152* (2013.01); *A61K 8/8176* (2013.01); *A61K 8/8182* (2013.01); *A61K 8/85* (2013.01); *A61Q 19/00* (2013.01); *A61Q 19/008* (2013.01); *A61K 2800/654* (2013.01); *A61K 2800/83* (2013.01)

(56) References Cited

FOREIGN PATENT DOCUMENTS

| | | |
|---|---|---|
| EP | 1370241 B1 | 11/2012 |
| FR | 2805743 A1 | 9/2001 |
| KR | 20020065959 A | 8/2002 |
| KR | 20020070154 A | 9/2002 |
| KR | 20020091779 A | 12/2002 |
| KR | 20040039501 A | 5/2004 |
| KR | 20070057333 A | 6/2007 |
| KR | 101015386 B1 | 2/2011 |
| KR | 20110046619 A | 5/2011 |
| KR | 20140110439 A | 9/2014 |
| KR | 101471280 B1 | 12/2014 |
| WO | 2011/068333 A2 | 6/2011 |
| WO | 2014/156994 A1 | 10/2014 |

OTHER PUBLICATIONS

International Search Report and Written Opinion for International Application No. PCT/KR2016/006882 (9 pages) (dated Oct. 25, 2016).

The extended European Search Report, Application No. 16818182.4, dated May 14, 2018.

\* cited by examiner

COMPOSITE POWDER IN WHICH JADE POWDER PARTICLES ARE IMPREGNATED IN POROUS POLYMER, COSMETIC COMPOSITION CONTAINING SAME AND MANUFACTURING METHOD FOR SAME

CROSS-REFERENCE TO RELATED APPLICATIONS

This application is a 371 of PCT/KR2016/006882, filed on Jun. 28, 2016 which claims the benefit of Korean Patent Application No. 10-2015-0092868, filed Jun. 30, 2015 and Korean Patent Application No. 10-2016-0080232, filed Jun. 27, 2016 the contents of each of which are incorporated herein by reference.

TECHNICAL FIELD

The present invention relates to a composite powder including jade powder and a porous polymer, and more particularly, to a composite powder (jade sphere) in which jade powder particles are impregnated in a porous polymer, the composite powder being manufactured by spraying a dispersion, in which jade powder is dispersed in a solution in which a porous polymer is dissolved, using a one-step process, a cosmetic composition containing the same, and a manufacturing method for the same.

BACKGROUND ART

When a composite powder in which two or more powders are combined is manufactured as a composite of organic powder and inorganic powder, a method for manufacturing a composite powder, which includes preparing underlying powder particles (A) and coating surfaces of the powder particles (A) with other powder particles (B), has been generally used. However, such technology has a drawback in that it has a complicated procedure due to a two-step manufacturing process, and also unique characteristics of the two or more powders may not be suitably exhibited. On the other hand, the method differs in that, when a spray drying process and an electro-spraying process are applied to a powdering method to manufacture a composite powder, a granular powder may be manufactured using a one-step process by uniformly dispersing the other powder particles (B) in the underlying powder particles (A) so that the other powder particles (B) permeate into the underlying powder particles (A).

Spray drying technology is a method that includes spraying a material in a dissolved state, which is composed of a raw material powder, a solvent, and a binder, using a spraying unit such as a nozzle or a rolling disk and instantly drying the dissolved material with hot wind. More specifically, the spray drying is a technique in which a granular product is directly obtained from a liquid raw material by atomizing a liquid raw material such as a solution, an emulsion, a dispersion, a suspension, a slurry, or the like to increase a surface area of the liquid raw material so as to increase a heat-receiving area, and instantly drying the liquid raw material through direct contact with a hot air current, and is characterized in that the drying and powdering are performed in a single step.

Therefore, because the contact of the products with heat is realized within several seconds, the spray drying has advantages in that it has a relatively small effect on physical properties of the products and the produced products may be easily handled. Therefore, the spray drying has been widely used to dry a natural extract and obtain granules when fine ceramics, milk powders, medicines, foods, dyes, and pigments are manufactured.

Korean Unexamined Patent Publication No. 2002-0091779 discloses a spray drying process, which includes spraying slurry including a raw material powder to form droplets and drying the droplets to obtain ceramic granules, thereby manufacturing a ceramic powder having excellent dispersing and filling properties. Korean Unexamined Patent Publication No. 2014-0110439 discloses a method for manufacturing a spherical boron nitride powder having a constant particle size using a spray drying technique.

Meanwhile, electro-spraying technology is a method for manufacturing fine particles, which includes injecting a polymer solution having certain electrical conductivity and viscosity through a capillary tube and applying an electrostatic force to the polymer solution. Generally, when the polymer solution is sprayed through a nozzle disposed in a vertical position, the balance between the gravity and the surface tension of the polymer solution is made at an end of the nozzle to form hemispherical drops so that the drops hang from the end of the nozzle. In this case, when an electric field is applied to the hemispherical drops, an orientation of charges or dipoles on surfaces of the hemispherical drops is induced at the interface between an air space and the solution, and a force opposing the surface tension is generated due to the repulsive power of such charges or dipoles. Therefore, a hemispherical surface of the end of the nozzle is stretched to form a conical surface referred to as a Taylor cone, and a charged polymer solution is released from the Taylor cone when the repulsive power of the charges or dipoles is greater than a force overcoming the surface tension. In this case, the polymer solution having low viscosity is sprayed in the form of fine drops due to the surface tension. Like the spray drying, the electro-spraying includes powdering the polymer solution in a single step.

The electro-spraying has advantages in that particles may be easily prepared due to a simple shape and structure of the device, the prepared particles may have a mono-dispersed distribution, and the electro-spraying is useful in manufacturing particles having various sizes ranging from several tens of nanometers to several hundreds of micrometers. Therefore, the electro-spraying has been widely used in the fields of thin film attachment, coating of a metal surface, mass and structural analyses of proteins and biochemical materials, and the like.

In recent years, research has been conducted to apply the electro-spraying to generation of particles including a drug in the field of drug delivery. For example, Registered Korean Patent No. 10-1471280 discloses a method for manufacturing ultrafine nanopowders of a poorly soluble substance, which includes electro-spraying a poorly soluble substance solution, which is prepared by dissolving a poorly soluble substance in an organic solvent and dispersing a surfactant in the resulting solution, in order to improve an in vivo absorption rate of the poorly soluble drug.

Considering that the spray drying and electro-spraying techniques may be useful in preparing a liquid raw material into granules through a one-step process, easily adjusting a particle size of the granules, and manufacturing spherical particles, the present inventors have developed a method of uniformly impregnating amorphous coarse jade powder particles in a porous polymer using spray drying and electro-spraying processes. Therefore, the present invention has been completed based on the facts.

PRIOR-ART DOCUMENT

Registered Korean Patent No. 10-1015386 entitled "Spray Dryer"

DISCLOSURE

Technical Problem

There are known techniques in which jade powder particles are included in a cosmetic composition for the purpose of a skin moisturizing or whitening effect, and the like. However, when the jade powder particles are formulated and applied onto the skin, the jade powder particles have a poor sense of feeling in use thereof because the jade powder particles have a coarse surface. Also, the jade powder particles have a drawback in that a white cast appears due to lumping of the jade powder particles, and whiteness may be degraded due to high chromaticness of jade itself when the jade powder particles are included in make-up cosmetics.

Technical Solution

To solve the above problems, according to one aspect of the present invention, there are provided a composite powder (hereinafter referred to as a jade sphere) in which jade powder particles are uniformly impregnated in a porous polymer by dispersing jade powder in a solution in which a porous polymer is dissolved, and then spraying the dispersion using a one-step spray drying or electro-spraying process, a cosmetic composition including the same, and a manufacturing method for the same.

The jade powder may have a particle size of 10,000 to 20,000 meshes, and may be impregnated at a content of 10 to 90% by weight, preferably 50 to 90% by weight, based on the total weight of the composite powder.

The porous polymer is preferably selected from the group consisting of poly(methyl methacrylate) (PMMA), poly (vinyl pyrrolidone) (PVP), poly(caprolactone) (PCL), and poly(L-lactic acid) (PLLA).

Advantageous Effects

When a jade sphere of the present invention in which jade powder particles are uniformly impregnated in a porous polymer is formulated as a cosmetic composition, the jade sphere has improved cosmetic durability due to a blue light-blocking effect of the jade powder and a sebum absorption powder of the porous polymer, compared to cosmetics including the jade powder alone.

Also, when an amorphous coarse jade powder is impregnated in a spherical porous polymer, the jade powder can be effective in improving applicability, spreadability and softness, preventing a white cast by solving a lumping phenomenon, and improving whiteness.

BEST MODE

The present invention relates to a composite powder including jade powder and a porous polymer, and more particularly, to a composite powder (hereinafter referred to as a jade sphere) in which jade powder particles are uniformly impregnated in a porous polymer by dispersing jade powder in a solution in which a porous polymer is dissolved, and then spraying the dispersion using a one-step spray drying or electro-spraying process, a cosmetic composition containing the same, and a manufacturing method for the same. In the present invention, the term 'impregnation' refers to a situation in which other powder particles are uniformly dispersed in underlying powder particles so that the other powder particles permeate into the underlying powder particles. In this case, such a configuration differs from a configuration in which surfaces of powder particles are coated with other powder particles or a configuration in which powder particles are supported between pores on surfaces of other powder particles, as known in the art. Hereinafter, the present invention will be described in detail.

Jade

Generally, jade is divided into jadeite jade and nephrite jade. Nephrite jade contains three minerals beneficial to the human body, that is, calcium (Ca), iron (Fe), magnesium (Mg) as main components unlike minor components such as sodium (Na) and aluminum (Al) contained in jadeite jade. Therefore, types of the jade powder applicable to the present invention are not limited. More preferably, the nephrite jade is used.

Also, Chuncheon jade used in the present invention is a kind of nephrite jade, that is, high-quality nephrite jade produced in the Chuncheon area of Gangwon-do. In this case, Chuncheon jade is an altered mineral of tremolite and actinolite of the amphibole family, which has a compact and delicate texture and also has a pilotoxitic texture with strong toughness.

In the present invention, jade is ground into powder, which is then used as the jade powder. As a conventional method performed by a person having ordinary skill in the art, a method of grinding nephrite jade into powder is not limited. However, the jade powder that may be used for a cosmetic composition according to the present invention is processed so that the jade powder particles have a particle size distribution of 10,000 to 20,000 meshes. When the particle size distribution is greater than 20,000 meshes, an effect of the jade powder may be not significant. On the other hand, when the particle size distribution is less than 10,000 meshes, a sense of feeling in use upon application to the skin may be degraded due to a coarse surface of the spherical jade sphere.

Porous Polymer

In the present invention, a porous polymer in which the jade powder particles are impregnated is in a spherical powdery phase having oil absorption and sebum absorption powder. For example, poly(methyl methacrylate) (PMMA) is used as the porous polymer. In addition, the porous polymer may be selected from the group consisting of poly(vinyl pyrrolidone) (PVP), poly(caprolactone) (PCL), and poly(L-lactic acid) (PLLA), but the prevent invention is not limited thereto.

Such a porous polymer is easily blended in the manufacture of various cosmetic formulations because the porous polymer has a spherical particle shape, and has excellent senses of feeling in use thereof, such as applicability, and the like because spherical particulates are rolled on the skin when the cosmetic formulations are applied onto the skin. Therefore, the porous polymer is generally often used in fundamental cosmetics for controlling sebum and make-up cosmetics for modifying a color tone of the skin due to surface characteristics of the spherical particulates, such as an effect of preventing greasiness of the skin using light scattering, and an effect of improving cosmetic durability.

Jade Sphere

In the jade sphere of the present invention, that is, a composite powder in which jade powder particles are uniformly impregnated in a porous polymer, the jade powder may be impregnated at a content of 10 to 90% by weight, more preferably impregnated at a content of 50 to 90% by weight, based on the total weight of the jade sphere. Also, the jade sphere may have an average particle diameter of 5 to 20 μm. Such characteristics of the jade sphere make the composite powder suitable for use as a cosmetic material in terms of an effect of the jade powder and a sense of feeling in use thereof upon application to the skin.

According to the present invention, the jade powder may be uniformly impregnated in the porous polymer by spray-drying or electro-spraying a porous polymer dispersion, in which the jade powder is dispersed in a porous polymer solution, to manufacture a jade sphere using a one-step process. In this case, an emulsifying agent is preferably excluded so that super-water repellency of the porous polymer can be achieved. The porous powder produced by a method known in the art, such as emulsion polymerization, has drawbacks in that the emulsifying agent irritates the skin because the use of the emulsifying agent is inevitable but the subsequent complete removal of the emulsifying agent is impossible, and the skin may get dry because the porous powder absorbs sebum of the skin as well as moisture. However, according to the present invention, there is no skin irritation caused by the emulsifying agent, only the sebum may be selectively absorbed due to super-water repellency, and cosmetic durability may be enhanced.

Also, the porous polymer solution may be obtained by dissolving poly(methyl methacrylate) (PMMA) in a mixed solvent of dichloromethane (DCM) and hexanol. In this case, a mixing ratio (weight ratio) of the dichloromethane (DCM) and hexanol may be chosen in a range of 9:1 to 7:3. In this case, the hexanol serves to form pores in the porous polymer. Therefore, it is not desirable because the size of the pores may be too small when the ratio of the hexanol is less than 10% by weight of the total solvent, whereas the size of the pores may be too high when the ratio of the hexanol is greater than 30% by weight of the total solvent.

In the present invention, porosity characteristics of the jade sphere may be controlled depending on conditions for a manufacturing process. The controllable porosity characteristics may include an average pore size, porosity, the total area of the pores, and the like. Specifically, the average pore size may be in a range of 15 to 800 nm, more preferably 250 to 600 nm, and the porosity may be in a range of 40 to 85%, more preferably 50 to 75%. Also, the total area of the pores may be in a range of 1 to 100 $m^2/g$, more preferably 5 to 80 $m^2/g$.

The jade sphere having such characteristics may be effective in enhancing an oil absorption rate due to the pore size and porosity. The oil absorption rate may be expressed as an intrusion volume of mercury to be described below. The intrusion volume of mercury in the jade sphere according to the present invention may be measured to be in a range of 0.5 to 5 $cm^3/g$, the value of which is at a reliable level so that the intrusion volume of mercury may be expressed as the oil absorption rate.

Conventional porous polymers have a relatively larger specific surface area but have a smaller average pore size and porosity due to a single-sized mesoporous structure, but the jade sphere of the present invention is much more advantageous in absorbing oils through a capillary action because pore channels are formed due to a multiporous (Micro+Meso+Macro) structure.

Cosmetic Composition

The jade sphere may be applied as a cosmetic composition. In this case, the jade sphere is preferably included at a content of 0.1 to 5.0% by weight, based on the total weight of the cosmetics. When the jade powder is present at an excessive content, the inherent natures or softness of raw materials for cosmetics, and a sense of feeling in use upon application to the skin may be degraded, and an increase in unit price of products may also be caused due to expensive jade. On the other hand, when the jade powder is present at a very small content, it is undesirable because it is impossible to expect effects caused by the jade powder.

Also, in addition to the jade powder, the cosmetic composition of the present invention may further include functional additives for improvement of skin conditions, such as improvement of skin wrinkles, improvement of skin whitening, improvement of skin elasticity, improvement of facial skin sagging, improvement of skin moisturizing, skin gloss improvement, skin aging prevention (e.g., inhibition of skin wrinkle formation and dermatosclerosis caused by photoaging), improvement of dark circles, and improvement of horny skin; functional additives for blocking ultraviolet (UV) rays; or components included in typical cosmetic compositions.

The functional additives for improvement of skin conditions may include components selected from the group consisting of water-soluble vitamins, fat-soluble vitamins, high-molecular-weight peptides, high-molecular-weight polysaccharides, sphingolipids, natural extracts, and fermented materials. Also, the functional additive for blocking UV rays may further include inorganic powders such as titanium dioxide ($TiO_2$), zinc oxide (ZnO), cerium oxide ($CeO_2$), and the like. In addition, the components included in the typical cosmetic compositions may be further blended together with the functional additives, when necessary.

Blending components included in addition to the aforementioned components may include oily components, moisturizing agents, emollients, surfactants, organic and inorganic pigments, organic powders, UV absorbing agents, preservatives, disinfectants, antioxidants, plant extracts, pH regulators, alcohols, dyes, fragrances, blood flow stimulants, cooling agents, anhydrotics, purified water, and the like, but the present invention is not limited thereto.

The cosmetic composition including the jade sphere may be formulated into any one form selected from toners, lotions, creams, sera, emulsions, nourishing sera, powders, foundations, sprays, sunscreen agents, mask packs, gels, and the like, more preferably may be formulated into mask packs, sheet packs, sleeping packs, wash-off packs, peel-off packs, and the like, but is not limited to the formulations. In this case, such formulations may be properly chosen and changed depending on a purpose.

MODE FOR INVENTION

Hereinafter, the present invention will be described in further detail with reference to specific embodiments thereof and the accompanying drawings. However, it will be apparent to those skilled in the art that the present invention is not limited to the embodiments disclosed below, but various modifications and changes can be made to the aforementioned embodiments of the present invention.

Components listed in the following Table 1 were prepared to manufacture composite powders of Examples 1 and 2 below.

TABLE 1

| Jade powder (Chuncheon jade) | Manufactured by Oksanga Co., Ltd. |
| Poly(methyl methacrylate) (PMMA) | Manufactured by LG PMMA |
| Dichloromethane anhydrous (DCM) | Manufactured by Sigma-Aldrich (Purity: >99.8%) |
| Hexanol (or 1-hexanol) | Manufactured by Sigma-Aldrich (Purity: >99%) |

Example 1

The components listed in Table 1 were prepared, and a jade sphere was manufactured according to the following spray drying method.

Spray Drying 1) 40 g of PMMA was dissolved in 1 L of a solvent (DCM:hexanol=9:1 (% by weight)).

2) 40 g of jade powder was added to the PMMA solution, and then dispersed using a homogenizer.

3) The PMMA solution in which the jade powder was dispersed was spray-dried according to the conditions listed in the following Table 2.

TABLE 2

| Inside moisture | 30% or more |
| Inside temperature | Maintained at room temperature |
| Inside pressure | 20 atm |
| Feed rate | 20% |
| Aspirator | 70% |

4) The PMMA solution in which the jade powder was dispersed was continuously stirred during the spray drying using a stirring machine.

5) The spray-dried jade powder/PMMA composite powder particles were thoroughly washed, and then freeze-dried to completely remove a residual solvent, thereby obtaining the jade powder/PMMA composite powder.

Example 2

The components listed in Table 1 were prepared, and a jade sphere was then manufactured according to the following electro-spraying method.

Electro-Spraying 1) 0.4 g of PMMA was dissolved in 10 mL of a solvent (DCM:hexanol=9:1 (% by weight)).

2) 0.4 g of jade powder was added to the PMMA solution, and then dispersed using a sonicator.

3) The PMMA solution in which the jade powder was dispersed was electro-sprayed according to the conditions listed in the following Table 3.

TABLE 3

| Inside moisture | 30% or more |
| Inside temperature | Maintained at room temperature |
| Distance | 15 cm |
| Feed rate | 20% |
| Voltage | 10 kV |

4) The electro-sprayed jade powder/PMMA composite powder particles were thoroughly washed, and then freeze-dried to completely remove a residual solvent, thereby obtaining the powder/PMMA composite powder.

Comparative Example 1

The jade powder listed in Table 1 was applied alone.

Figure 1:
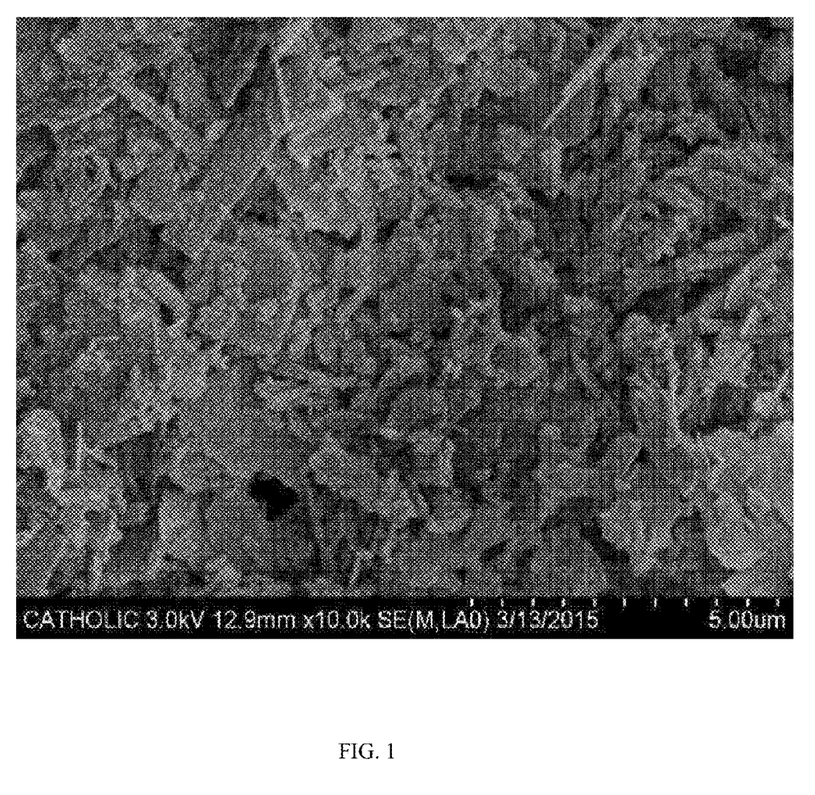
FIG. 1 is a scanning electron microscope (SEM) image of a jade powder applied to the present invention.
Figure 2:
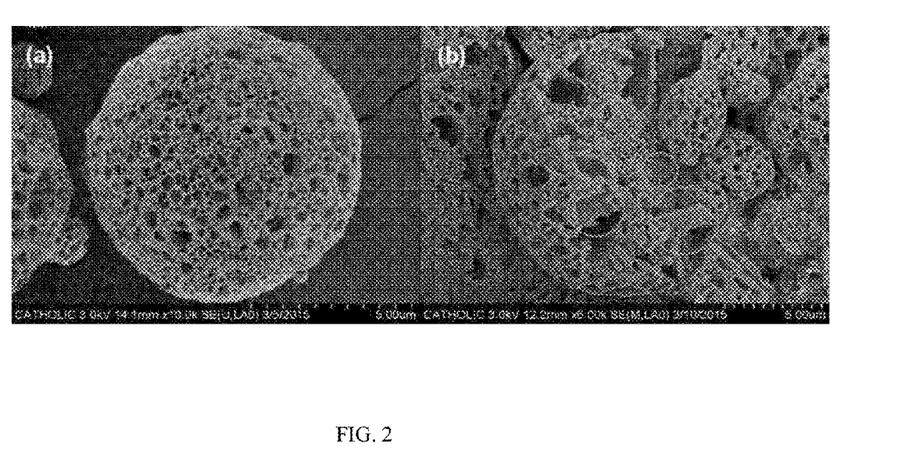
FIG. 2 is a scanning electron microscope (SEM) image of a jade sphere of the present invention: (A) is an image of a surface of the jade sphere, and (B) is an image of a cut-off plane of the jade sphere.

FIG. 1 is a scanning electron microscope (SEM) image of the jade powder of Comparative Example 1, and FIG. 2 is a scanning electron microscope (SEM) image of (A) a surface and (B) a cut-off plane of a jade sphere of Example 1 in which such a jade powder is uniformly impregnated in poly(methyl methacrylate) (PMMA) particles as a porous polymer. As shown in FIG. 1, as particles having an amorphous coarse structure, the jade powder was subjected to spray drying and electro-spraying methods so that the jade powder was uniformly impregnated in the poly(methyl methacrylate)(PMMA) particles as shown in FIG. 2.

Figure 3:
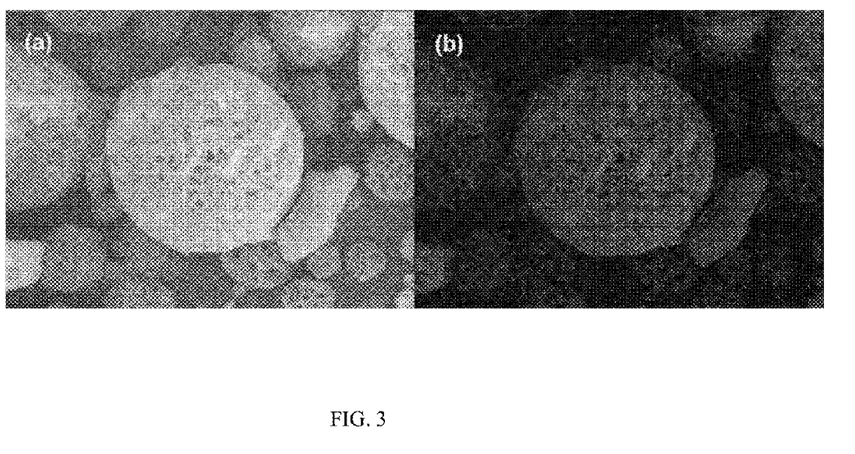
FIG. 3 is an image of the jade sphere of the present invention quantitatively and qualitatively analyzed using an energy dispersive X-ray (EDX) spectrometer: (A) is an image of a surface of the jade sphere, and (B) is an image of individual elements included in the jade sphere after the elements are visualized.

FIG. 3 is an image of the jade sphere of Example 1 quantitatively and qualitatively analyzed using an energy dispersive X-ray (EDX) spectrometer: (A) is an image of the jade sphere of Example 1, and (B) is an image of individual elements included in the jade sphere after the elements are visualized by points. As main components of Chuncheon jade used in the present invention, calcium (Ca, Red point) and magnesium (Mg, Blue point) ions were confirmed. As a result, it can be seen that the jade powder was distributed so that the jade powder was uniformly impregnated in the whole poly(methyl methacrylate) (PMMA).

Tests on Items

Hereinafter, tests on items of the jade sphere manufactured by the spray drying method were carried out.

<Experimental Example 1> Reflectance Test

The reflectance spectra of subjects for tests were measured at a wavelength range of 360 to 740 nm using a color difference meter (ColorMate commercially available from Scinco Co., Ltd., Korea). Then, PC software, ColorMaster, was used to measure the reflectance. The reflectance was measured to calculate a light blocking rate in the corresponding spectrum.

Figure 4:
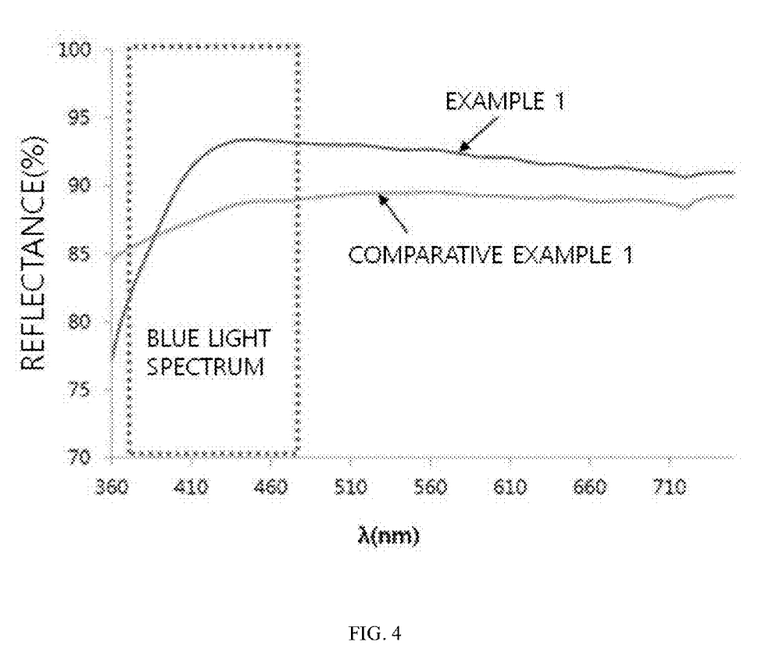
FIG. 4 shows test results of reflectance (%) of the jade sphere of the present invention in the visible light spectrum.

As shown in FIG. 4, it was revealed that both of the jade powder of Comparative Example 1 and the jade sphere of Example 1 had high reflectance in the visible light spectrum (380 to 710 nm), particularly that the jade sphere of Example 1 had higher reflectance in a long wavelength range of 380 nm or more, compared to the jade powder of Comparative Example 1. In particular, it can be seen that the jade sphere of Example 1 had a high difference in the reflectance of light in the blue light spectrum (380 to 500 nm), indicating that the jade sphere of Example 1 had a blue light-blocking rate higher than the jade powder of Comparative Example 1.

<Experimental Example 2> Whiteness (% R) Test

Whiteness is a value that one-dimensionally represents a degree of white color. In the reflectance test, a whiteness index was calculated based on XYZ color difference values in the entire visible light spectrum using the following equation.

$$WI=Y+800(x_n-x)+1,700(y_n-y) < CIE \text{ Whiteness}>$$

$X_n$=0.3101, $Y_n$=0.3162 (C/2°), $X_n$=0.3138, $Y_n$=0.3309 (C/2°)

Figure 5:
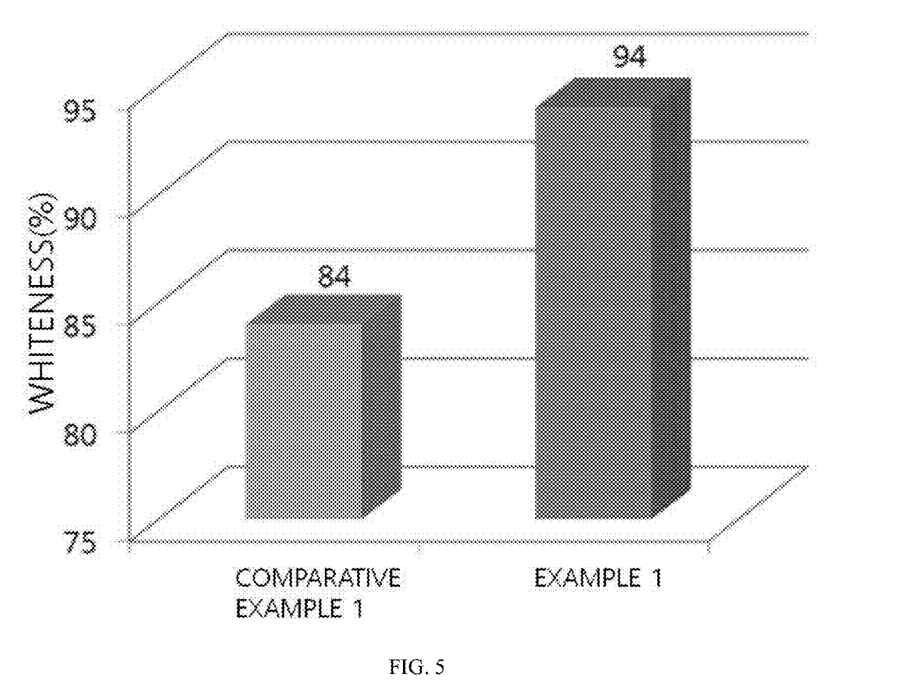
FIG. 5 shows test results of whiteness (% R) of the jade sphere of the present invention.

As shown in FIG. 5, it was revealed that the jade sphere of Example 1 had a whiteness of 94%, which was improved by 10%, compared to the jade powder of Comparative Example 1 having a whiteness of 84%.

<Experimental Example 3> Porosity Measurement Test

To analyze porosity characteristics of the jade sphere of Example 1, a mercury (Hg) intrusion assay was performed. The intrusion volume of mercury, average pore size (4V/A, V: volume, and A: area) and porosity were measured using a porosimeter (Autopore IV 9500, Micrometrics, Londonderry, N.H., USA). The results are listed in Table 4.

TABLE 4

| | |
|---|---|
| Total intrusion volume | 1.6797 mL/g |
| Total pore area | 15.125 m²/g |
| Average pore diameter (4 V/A) | 444.2 nm |
| Bulk density at 0.20 psia | 0.3832 g/mL |
| Porosity | 64.37% |

The term 'total intrusion volume' refers to an amount of mercury intruded per unit gram, the term 'total pore area' refers to a total pore area expressed as a cylindrical area, the term 'average pore diameter' refers to an average value of the total pore sizes, and the term 'bulk density at 0.20 psia' refers to a true density of a sample including pores at 0.20 psia.

As a result, it can be seen that the jade sphere of Example 1 had an average pore size of 444.2 nm and a high porosity of 64.37%.

<Experimental Example 4> Oil Absorption Test

One gram of the jade sphere of Example 1 was weighed using a scale and a Petri dish, and an absorption rate of oil required until the jade sphere of Example 1 got wet by dropping triglyceride oil having physical properties similar to the human sebum using a spuit was measured. In this case, the oil was stirred with a spatula so that the jade sphere of Example 1 was sufficiently wet with the oil.

Figure 6:
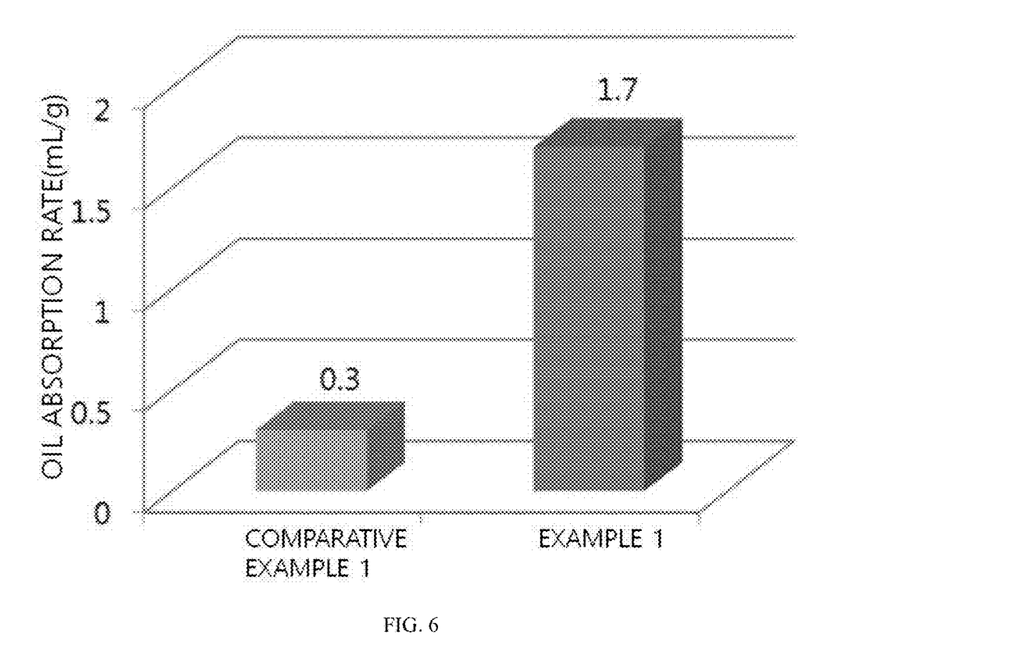
FIG. 6 shows test results of an oil absorption rate (mL/g) of the jade sphere of the present invention.

As shown in FIG. 6, it can be seen that the jade sphere of Example 1 had an oil absorption rate of 1.7 mL/g, which was very similar to the total intrusion volume (1.6797 mL/g) of mercury in the porosity measurement test of Experimental Example 3, which proved the reliability of the results of measurement of the oil absorption rate. Also, it can be seen that the oil absorption rate of the jade sphere of Example 1 increased by up to 5 times, compared to the jade powder. This was an effect obtained when the jade sphere of Example 1 had a large pore size and high porosity although the jade sphere of Example 1 included the jade powder at 50% by weight.

Hereinafter, the jade sphere manufactured in Example 1 was formulated into the form of an emulsion (for mask packs) based on the compositions (% by weight) listed in the following Table 5, and tests on items was then performed.

TABLE 5

| Items | Component | Comparative Formulation Example 1 | Comparative Formulation Example 2 | Formulation Example 1 |
|---|---|---|---|---|
| Oily phase part | Cetearyl alcohol | 4.00 | 4.00 | 4.00 |
| | Stearic acid | 0.50 | 0.50 | 0.50 |
| | Palmitic acid | 0.50 | 0.50 | 0.50 |
| | Hydrogenated lecithin | 1.00 | 1.00 | 1.00 |
| | Glyceryl stearate | 1.50 | 1.50 | 1.50 |
| | Triethylhexanoin | 3.00 | 3.00 | 3.00 |
| | Pentaerythrityl tetraethylhexanoate | 4.00 | 4.00 | 4.00 |
| | Trisiloxane | 2.00 | 2.00 | 2.00 |
| | Dimethicone | 2.00 | 2.00 | 2.00 |
| Aqueous phase part | fragrance | Proper amount | Proper amount | Proper amount |
| | purified water | Proper amount | Proper amount | Proper amount |
| | Disodium EDTA | 0.05 | 0.05 | 0.05 |
| | Glycerin | 4.00 | 4.00 | 4.00 |
| | Propanediol | 10.00 | 10.00 | 10.00 |
| | Other thickening and neutralizing agents | Proper amount | Proper amount | Proper amount |
| | preservative | Proper amount | Proper amount | Proper amount |
| | Chuncheon jade | 0.00 | 1.00 | 0.00 |
| | Jade Sphere | 0.00 | 0.00 | 1.00 |

<Experimental Example 5> Usability Evaluation Test

Thirty women of age from 25 to 35 years used the formulations of Comparative Formulation Examples 1 and 2 and Formulation Example 1 of the present invention twice a day for a month. Thereafter, the usability of the formulations as the cosmetics was evaluated in scores ranging from 1 to 5 by comparing the items such as adhesion, spreadability, softness, particle lumping, cosmetic durability, and the like. The results are listed in the following Table 6.

TABLE 6

| Items | Adhesion | Spreadability | Softness | Particle lumping | Cosmetic durability |
|---|---|---|---|---|---|
| Comparative Formulation Example 1 | 5 | 5 | 5 | 1 | 3 |
| Comparative Formulation Example 2 | 2 | 3 | 2 | 5 | 2 |
| Formulation Example 1 | 4 | 4 | 5 | 2 | 5 |

Looking at Table 6, it was revealed that the formulation of Comparative Formulation Example 2 including the Chuncheon jade powder had higher particle lumping and lower estimation values for all the items including adhesion, spreadability, softness and cosmetic durability, compared to the formulation of Comparative Formulation Example 1 including no jade powder. On the other hand, it was revealed that the formulation of Formulation Example 1 including the jade sphere had significantly reduced particle lumping and improved adhesion and spreadability, compared to the formulation of Comparative Formulation Example 2 including the Chuncheon jade powder, and had similar or improved softness and cosmetic durability, compared to the formulation of Comparative Formulation Example 1.

Therefore, the jade sphere of the present invention had excellent outcomes such as softness derived from the spherical shape thereof, and cosmetic durability derived from the oil absorption of sebum caused due to high porosity thereof. Also, it can be seen that a white cast may be prevented by significantly improving the particle lumping which had been considered as the biggest problem of the formulation of Comparative Formulation Example 2 including the jade powder.

<Experimental Example 6> Reflectance Test of Formulation

To measure light-blocking rates of the formulations of Comparative Formulation Examples 1 and 2 and Formulation Example 1 in the visible light spectrum, the reflectance spectra of subjects for tests were measured at a wavelength range of 360 to 740 nm using a color difference meter (ColorMate commercially available from Scinco Co., Ltd., Korea). Then, PC software, ColorMaster, was used to measure the reflectance.

Figure 7:
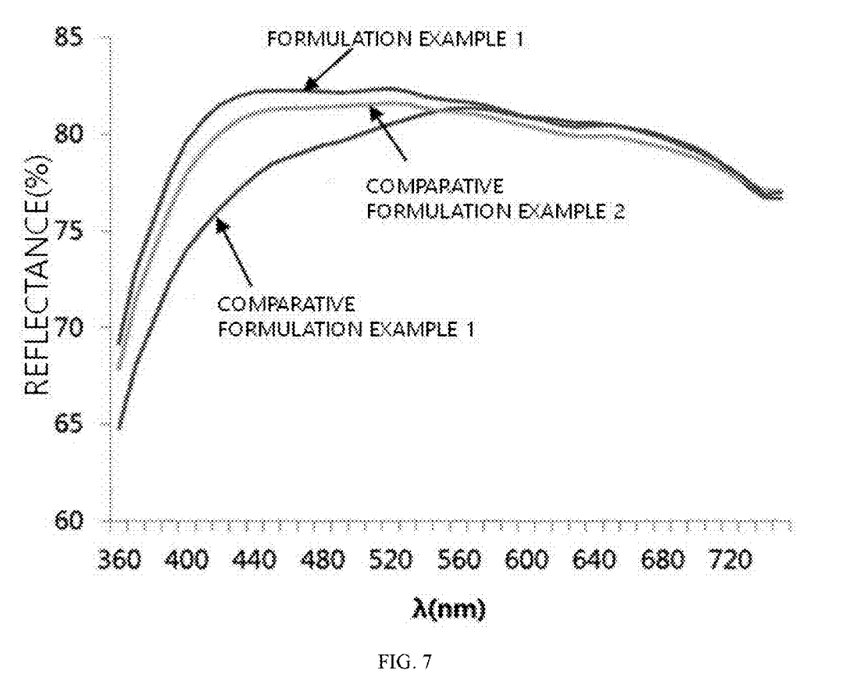
FIG. 7 shows test results of reflectance (%) of formulations including the jade sphere of the present invention in the visible light spectrum.

As shown in FIG. 7, it was revealed that all the manufactured formulations of Comparative Formulation Examples 1 and 2 and Formulation Example 1 had outcomes similar to the results of the reflectance tests performed on the jade spheres in a powdery state. In particular, it can be seen that the jade sphere of Preparative Example 1 had a high difference in the reflectance of light with shorter wavelengths in the blue light spectrum, indicating that the jade sphere had a high blue light-blocking rate even when prepared into formulations.

<Experimental Example 7> Whiteness (% R) Test of Formulations

Whiteness of a formulation is a value that one-dimensionally represents a degree of white color. In the reflectance test of the formulation, a whiteness index was calculated based on XYZ color difference values in the entire visible light spectrum using the following equation.

$$WI = Y + 800(x_n - x) + 1{,}700(y_n - y) < CIE\ \text{Whiteness}>$$

$X_n = 0.3101$, $Y_n = 0.3162$ (C/2°), $X_n = 0.3138$, $Y_n = 0.3309$ (C/2°)

Figure 8:
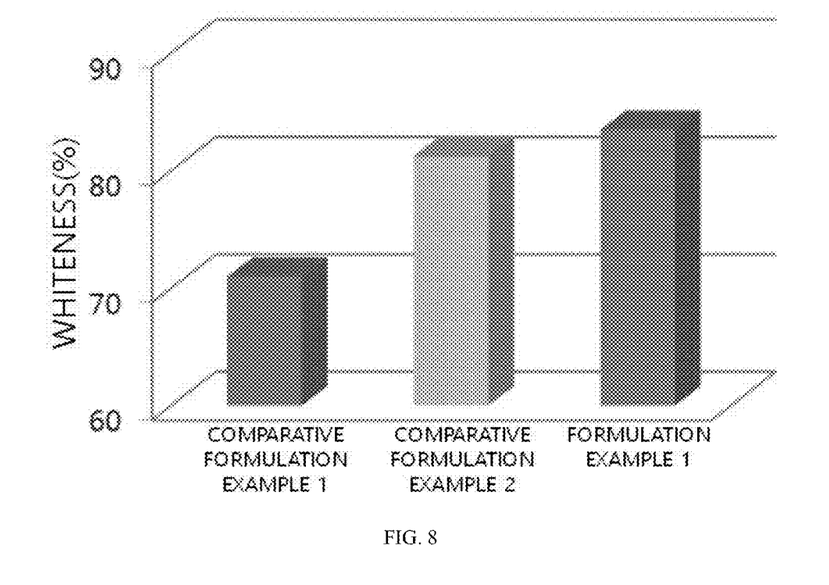
FIG. 8 shows test results of whiteness (% R) of the formulations including the jade sphere of the present invention.

As shown in FIG. 8, it can be seen that the whiteness of each of the formulations of Comparative Formulation Example 2 and Formulation Example 1 including the jade powder or jade sphere was significantly improved, compared to the formulation of Comparative Formulation Example 1 including no jade powder. Here, it was revealed that the jade sphere of Formulation Example 1 had the highest whiteness although there was a slight difference in whiteness between the formulations.

Formulation Example 2

Hereinafter, a face lotion containing 0.1% by weight of the jade sphere manufactured in Example 1 was manufactured based on the compositions (% by weight) listed in the following Table 7 using a conventional method.

TABLE 7

| Component | content (% by weight) |
|---|---|
| Purified water | Balance |
| Glycerin | 8.0 |
| Butylene glycol | 4.0 |
| Hyaluronic acid extract | 5.0 |
| β-Glucan | 7.0 |
| Carbomer | 0.1 |
| Glucoceramide & 7,8,4'-trihydroxyisoflavone | 0.05 |
| Caprylic/capric triglyceride | 8.0 |
| Squalane | 5.0 |
| Cetearyl glucoside | 1.5 |
| Sorbitan stearate | 0.4 |
| Cetearyl alcohol | 1.0 |
| Triethanolamine | 0.1 |
| Jade Sphere | 0.1 |

Formulation Example 3

Hereinafter, a nourishing cream containing 3.0% by weight of the jade sphere manufactured in Example 1 was manufactured based on the compositions (% by weight) listed in the following Table 8 using a conventional method.

TABLE 8

| Component | Content (% by weight) |
|---|---|
| Purified water | Balance |
| Glycerin | 3.0 |
| Butylene glycol | 3.0 |
| Liquid paraffin | 7.0 |
| B-glucan | 7.0 |
| Carbomer | 0.1 |
| Glucoceramide & 7,8,4'-trihydroxyisoflavone | 3.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Jade sphere | 3.0 |

Formulation Example 4

Hereinafter, a massage cream containing 5.0% by weight of the jade sphere manufactured in Example 1 was manufactured based on the compositions (% by weight) listed in the following Table 9 using a conventional method.

TABLE 9

| Component | Content (% by weight) |
|---|---|
| Purified water | Balance |
| Glycerin | 8.0 |
| Butylene glycol | 4.0 |
| Liquid paraffin | 45.0 |
| B-glucan | 7.0 |
| Carbomer | 0.1 |
| Glucoceramide & 7,8,4'-trihydroxyisoflavone | 1.0 |
| Caprylic/capric triglyceride | 3.0 |
| Wax | 4.0 |
| Cetearyl glucoside | 1.5 |
| Sorbitan sesquioleate | 0.9 |
| Vaseline | 3.0 |
| Paraffin | 1.5 |
| Jade sphere | 5.0 |

The invention claimed is:

1. A composite powder in which jade powder particles are impregnated in a porous polymer,
wherein the jade powder particles are impregnated at a content of 50 to 90% by weight, based on the total weight of the composite powder,
wherein the porous polymer comprises poly(methyl methacrylate) (PMMA),
wherein the composite powder has an average pore size of 250 to 600 nm, and
wherein the composite powder has a porosity of 40 to 85%.

2. The composite powder of claim 1, wherein the composite powder has an average particle diameter of 5 to 20 µm.

3. A cosmetic composition comprising the composite powder of claim 1.

4. The cosmetic composition of claim 3, wherein the composite powder is included at a content of 0.1 to 5.0% by weight, based on the total weight of the cosmetic composition.

5. The cosmetic composition of claim 3, wherein the cosmetic composition is formulated into any one form selected from the group consisting of a toner, a lotion, a cream, a serum, an emulsion, a nourishing serum, a powder, a foundation, a spray, a sunscreen agent, a mask pack, and a gel.

6. A method for manufacturing a composite powder according to claim 1 in which jade powder particles are impregnated in a porous polymer comprising:
spray-drying or electro-spraying a dispersion in which jade powder is dispersed in a porous polymer solution to manufacture the composition powder; wherein the porous polymer is poly(methyl methacrylate) (PMMA).

7. The method of claim 6, wherein the porous polymer solution is obtained by dissolving poly(methyl methacrylate) (PMMA) in a solvent, and the solvent is a mixed solvent of dichloromethane and hexanol.

8. The method of claim 7, wherein the dichloromethane and the hexanol are present at a weight ratio of 9:1 to 7:3.

* * * * *